United States Patent
Jung et al.

(10) Patent No.: US 6,965,045 B2
(45) Date of Patent: Nov. 15, 2005

(54) ORGANIC METAL PRECURSOR FOR USE IN FORMING METAL CONTAINING PATTERNED FILMS

(75) Inventors: Won Cheol Jung, Seoul (KR); Seok Chang, Daejun-Shi (KR); Soon Taik Hwang, Kyungki-Do (KR); Young Hun Byun, Daejun-Shi (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 211 days.

(21) Appl. No.: 10/282,031

(22) Filed: Oct. 29, 2002

(65) Prior Publication Data

US 2003/0124457 A1 Jul. 3, 2003

(30) Foreign Application Priority Data

Dec. 28, 2001 (KR) .......................... 2001-87510

(51) Int. Cl.[7] .............................. C07F 1/00; C07F 15/00
(52) U.S. Cl. ........................ 556/113; 556/130; 556/136; 556/146
(58) Field of Search ................................ 556/113, 130, 556/136, 146

(56) References Cited

U.S. PATENT DOCUMENTS 5,064,685 A  11/1991  Kestenbaum et al. ...... 427/53.1
5,534,312 A   7/1996  Hill et al. .................. 427/533

FOREIGN PATENT DOCUMENTS

JP  62-263973 A  11/1987

OTHER PUBLICATIONS

El–Etri et al., Inorganica Chimica Acta, vol. 187, pp. 201–206 (1991).*

* cited by examiner

*Primary Examiner*—Porfirio Nazario-Gonzalez
(74) *Attorney, Agent, or Firm*—Birch, Stewart, Kolasch & Birch, LLP

(57) ABSTRACT

An organic metal precursors containing one or more organic ligands bonded to one or more metal atoms, wherein the organic ligand is rapidly dissociated from the metal atom upon exposure to light and degraded leaving a metal or a metal oxide. By using the organic metal precursors, an electroconductive, metal-containing patterned film can be easily deposited on a substrate at room temperature under atmospheric pressure without using photosensitive resins.

2 Claims, 1 Drawing Sheet

ORGANIC METAL PRECURSOR FOR USE IN FORMING METAL CONTAINING PATTERNED FILMS

This non-provisional application claims priority under 35 U.S.C. § 119(a) on Patent Application No. 2001-87510 filed in Korea on Dec. 28, 2001, which is herein incorporated by reference.

BACKGROUND OF THE INVENTION

1. Field of the Invention

The present invention relates, in general, to an organic metal precursor and a method for forming a metal-containing patterned film on a substrate using the same, and in detail, to an organic metal precursor that enables an electroconductive metal pattern of a micro- or nano-scale to be shaped only by the aid of light without using separate photoresists. The present invention is also directed to a method for depositing a patterned film of a metal or a metal oxide on a substrate via a photo-induced chemical reaction of the organic metal precursor.

2. Background Art

Conventionally, patterned films of metal-containing materials have been made through complicated process involving: depositing a film of an organic metal compound on a silicon or glass substrate by chemical vapor deposition or atomic layer deposition; applying a photoresist film on the organometallic film by spin-coating; and patterning and etching the photoresist film by photolithography. Alternatively, a film of a metal may be deposited on a substrate through plasma deposition, sputtering or electroplating and then coating with a photosensitive resinous film, followed by patterning with light and etching of the resinous film to afford a patterned film of the metal. Unfortunately, these prior techniques generally require high temperature and high vacuum conditions and involve the laborious steps of patterning and etching the films of the photosensitive resin.

Other techniques for forming metallic patterned films have been also proposed which do not depend on photochemical reactions. For example, Japanese Laid-Open Publication No. 62-263973 discloses a patterning method wherein electron beam is irradiated to a thin film of an organometallic compound. In U.S. Pat. No. 5,064,685, organometallic compound-containing ink is applied to a substrate, and then the resulting coating film is allowed to undergo thermal-degradation by being exposed to laser beam radiation to provide a patterned film of a metal. According to this method, the substrate should be subjected to a high temperature condition, and only metal can be deposited.

On the other hand, U.S. Pat. No. 5,534,312 describes that a pattern of a metal can be made through coating a substrate with a metal complex prepared by bonding one or more photosensitive organic ligands to one or more metal atoms, and exposing the substrate to electromagnetic radiation, wherein there is no necessity for applying a photosensitive resin to the coating film of the metal complex. The metal complex consists essentially of at least one ligand selected from the group consisting of: acetylacetonates (both substituted and unsubstituted); dialkyldithiocarbamates; carboxylates; pyridines; amines; diamines; arsines; diarsenes; phosphines; diphosphenes; arenes; alkoxy ligands; alkyl ligands; and aryl ligands. Particularly, in the case where the complex comprises more than one ligand, at least one of the ligands is selected from the group consisting of: oxalato; halogens; hydrogen; hydroxy; cyano; carbonyl; nitro; nitrito; nitrate; nitrosyl; ethylenes; acetylenes; thiocyanato; isothyocyanato; aquo; azides; carbonato; amines; and, thiocarbonyl. When exposed to electromagnetic radiation, the metal complex goes through a photochemical reaction resulting in dissociation of the organic ligands from the central metal atoms, to produce a new metal-containing material adherent to the substrate. However, the rate of such transformation is relatively low, and consequently many hours are required to complete the patterning process, which is the critical problem with this technique.

SUMMARY OF THE INVENTION

The present invention relates to an organic metal precursor comprising one or more organic ligands bonded to one or more metal atoms, wherein the organic ligand is rapidly dissociated from the metal atom upon exposure to light to significantly reduce the patterning time, and to the use of the organic metal precursor.

In one aspect of the present invention, there is provided an organic metal precursor compound represented by the formula (I):

wherein M is a transition metal atom selected from the group consisting of

Ag, Au, Co, Cu, Pd, Ni, Pt, Zn and Cd;
L is a thioether represented by the formula (II) or (III);

wherein in formula (II), each of $R_1$ and $R_2$, independently, is a $C_{1-20}$ straight-chain, branched-chain or cyclic alkyl, alkenyl or alkynyl group, or an allyl group;

in the formula (III), each of $R_3$ and $R_4$, independently, is a hydrogen atom, or a $C_{1-15}$ straight-chain or branched-chain alkyl group, and y is an integer from 2 to 10;

L' is a ligand selected from the group consisting of amines, thiols, selenols and phosphines;
X is an anion selected from the group consisting of halogeno, hydroxide (OH$^-$), cyanide (CN$^-$), nitroxyl (NO$^-$), nitrite (NO$_2^-$), nitrate (NO$_3^-$), azide (N$_3^-$), thiocyanato, isothiocyanato, tetraalkylborate, tetrahaloborate, hexafluorophosphate (PF$_6^-$), triflate (CF$_3$SO$_3^-$), tosylate (Ts$^-$), sulfate (SO$_4^{2-}$), and carbonate (CO$_3^{2-}$); and
each of m and n, independently, is an integer of from 1 to 10; and
each of o and p, independently, is an integer of from 0 to 10.

In the other aspect of the present invention, there is provided a method for forming a pattern of a metal or a metal oxide on a substrate comprising the steps of:

depositing a film of an organic metal precursor on a surface of the substrate;

placing a photomask of a desired pattern on the film and exposing unmasked areas of the film to a light source to cause the organic metal precursor in the unmasked area to be decomposed resulting in a patterned film of a metal or a metal oxide; and washing the substrate with an organic developer capable of dissolving the organic metal precursor to remove the remaining organic metal precursor in the masked areas leaving only the patterned film of a metal or a metal oxide.

All of the above features and other features of the present invention will be successfully achieved from the present invention described in the following.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
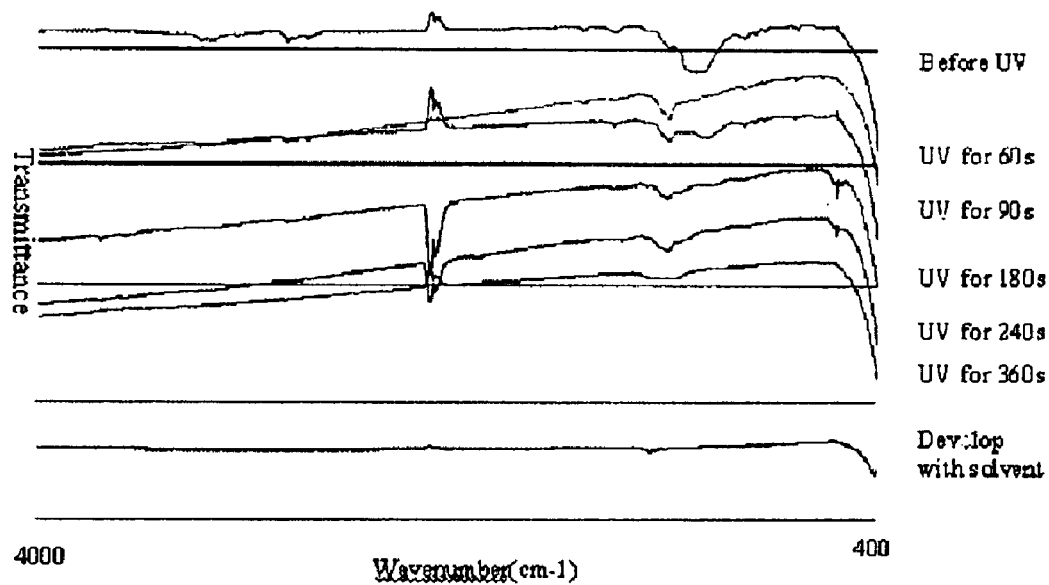
FIG. 1 is a graph showing the degradation rate of the organic metal precursor prepared according to the Example 4 by the exposure to light.

The organic metal precursors of the present invention are represented by the formula (I):

$$M_m L_n L'_o X_p \quad (I)$$

wherein, M is a transition metal atom selected from the group consisting of Ag, Au, Co, Cu, Pd, Ni, Pt, Zn and Cd;
L is a thioether represented by the formula (II) or (III);

(II)

wherein in formula (II), each of $R_1$ and $R_2$, independently, is a $C_{1-20}$ straight-chain, branched-chain or cyclic alkyl, alkenyl or alkynyl group, or an allyl group;

(III)

in the formula (III), each of $R_3$ and $R_4$, independently, is a hydrogen atom, or a $C_{1-15}$ straight-chain or branched-chain alkyl group, and y is an integer from 2 to 10;
L' is a ligand selected from the group consisting of amines, thiols, selenols and phosphines;
X is an anion selected from the group consisting of halogeno, hydroxide ($OH^-$), cyanide ($CN^-$), nitroxyl ($NO^-$), nitrite ($NO_2^-$), nitrate ($NO_3^-$), azide ($N_3^-$), thiocyanato, isothiocyanato, tetraalkylborate, tetrahaloborate, hexafluorophosphate ($PF_6^-$), triflate ($CF_3SO_3^-$), tosylate ($Ts^-$), sulfate ($SO_4^{2-}$), and carbonate ($CO_3^{2-}$); and
each of m and n, independently, is an integer of from 1 to 10; and
each of o and p, independently, is an integer of from 0 to 10.

The organic ligands constituting the organic metal precursor of the present invention are so photosensitive as to be rapidly dissociated and degraded from the central metal atoms upon exposure to light, producing a metal or a metal oxide which adheres to a surface of a substrate. Therefore, the use of the organic metal precursor of the present invention makes the troublesome steps of applying and etching a separate film of a photosensitive resin avoidable.

In order to form a metal-containing patterned film on a substrate using the organic metal precursors of the present invention, an organic metal precursor is first dissolved in a suitable organic solvent to provide a coating solution. The coating solution is applied to the surface of a substrate to form a film of the organic metal precursor on the substrate. The substrate used in the present invention includes, without limitation, substrates made of inorganic materials such as silicon and glass, as well as substrates made of organic materials such as plastic. Substrates produced by using organic and inorganic materials in combination can be also used. Preferably, the coating step can be accomplished through spin coating, roll coating, micro-contact printing, or spray coating. With a photomask of a desired pattern placed on the coating film, the film is then exposed to a light source, preferably ultraviolet light. Finally, the film is developed with an organic solvent capable of dissolving the organic metal precursor, which can be the same as or different from the organic solvent used in the preparation of the coating solution.

During the exposure, the organic metal precursor in the unmasked areas of the film is certain to undergo a photochemical reaction, where the organic ligands, L and L' dissociate from the central metal atom, M and then degrade. Particularly, upon exposure to light having an appropriate wavelength, the thioether ligand, L dissociates from the central metal atom more rapidly as compared with any other organic ligands. This was verified by means of an infrared spectrometer. An investigation of the degree of ligand dissociation according to the irradiation time revealed that most of the organic ligands (including L and L') dissociated from the central metal atoms in 4 minutes after the irradiation. As a result of such decomposition of the precursor compound, the organic metal precursor in the exposed areas of the film is rapidly converted into a corresponding metal, or is frequently converted into the corresponding metal oxide by the action of atmospheric oxygen. In addition to this advantageous dissociation property, the thioether ligand makes the solubility of the organic metal precursor of the present invention so improved as to quickly dissolve in any of the conventional organic solvents. The dissociated organic ligands are also easily washed off with an organic solvent in the subsequent developing step together with the unexposed areas of the film as described above, to provide a patterned film of a metal or a metal oxide.

The method for forming a metal-containing patterned film according to the present invention may further comprise oxidizing, reducing and/or annealing the patterned film for the purpose of enhancing general film properties including conductivity and adhesiveness to a substrate. The annealing is preferably carried out at a relatively low temperature below 300° C., preferably below 200° C. in an atmosphere of $H_2/N_2$ mixed gas, $N_2$ gas or air, so that any adverse effect of heat on the substrate can be prevented. If necessary, the annealing may be carried out in the presence of a suitable oxidant or reductant for the purpose of further oxidizing or reducing the metal or the metal oxide in the pattered film, respectively.

The patterning method of the present invention may be substituted for the sputtering process required in manufacturing the conventional flexible displays and flat panel displays, and may be adapted for the CMP-free damascene processing and the PR-free ITO film deposition.

The present invention can be more clearly understood with referring to the following examples. It should be understood that the following examples are not intended to restrict the scope of the present invention in any manner.

EXAMPLE 1

Synthesis of Tetrahydrothiophene Silver Nitrate

To a 100 ml round bottom flask was sequentially added 10 mmol (1.69 g) of silver nitrate ($AgNO_3$) and 20 ml of acetonitrile ($CH_3CN$), followed by stirring at room temperature for 5 minutes. Next, 10 mmol (0.88 g, 0.88 ml) of tetrahydrothiophene was dropwise added to the flask by means of a syringe over 10 seconds and stirred at room temperature. After stirring for 30 minutes, the reaction mixture was warmed to 50° C. and further stirred for 30 minutes. Following cooling to room temperature, the reaction mixture was filtered through a microfilter and evaporated under vacuum to produce a white solid matter. $^1$H-NMR result in $CD_3CN$ is as follows: 2.01 (m, 4H), 2.98(m, 4H).

EXAMPLE 2

Synthesis of Diethylthioether Silver Nitrate

To a 100 ml round bottom flask was sequentially added 10 mmol (1.69 g) of silver nitrate and 20 ml of acetonitrile, followed by stirring at room temperature for 5 minutes. Next, 10 mmol (0.90 g, 1.08 ml) of diethylthioether was dropwise added to the flask by means of a syringe over 10 seconds and stirred at room temperature. After stirring for 30 minutes, the reaction mixture was warmed to 50° C. and further stirred for 30 minutes. Following cooling to room temperature, the reaction mixture was filtered through a microfilter and evaporated under vacuum to produce a pale ivory solid matter. $^1$H-NMR result in $CD_3CN$ is as follows: 1.34 (t, 7.36 Hz, 6H), 2.76(q, 7.36 Hz, 4H).

EXAMPLE 3

Synthesis of Diethylthioether Silver Nitrite

To a 100 ml round bottom flask was sequentially added 10 mmol (1.54 g) of silver nitrite ($AgNO_2$) and 20 ml of acetonitrile, followed by stirring at room temperature for 5 minutes. Next, 10 mmol (0.90 g, 1.08 ml) of diethylthioether was dropwise added to the flask by means of a syringe over 10 seconds and stirred at room temperature. After stirring for 30 minutes, the reaction mixture was warmed to 50° C. and further stirred for 30 minutes. Following cooling to room temperature, the reaction mixture was filtered through a microfilter and evaporated under vacuum to produce a pale yellow solid matter. $^1$H-NMR result in $CD_3CN$ is as follows: 1.31 (t, 7.34 Hz, 6H), 2.72 (broad q, 7.35 Hz, 4H).

EXAMPLE 4

Synthesis of Bis (n-Propylamine Silver) Diethylthioether Dinitrite

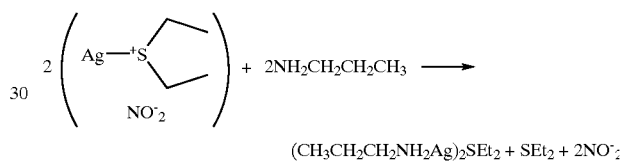

To a 100 ml round bottom flask was sequentially added 10 mmol (2.44 g) of diethylthioether silver nitrite obtained from the above Example 3 and 30 ml of acetonitrile, followed by stirring at room temperature for 5 minutes. Subsequently, 10 mmol (0.60 g, 0.82 ml) of n-propylamine was dropwise added to the flask by means of a syringe over 10 seconds and stirred at room temperature. After stirring for 60 minutes, the reaction mixture was filtered through a microfilter and evaporated under vacuum to produce a pale yellow solid matter. $^1$H-NMR result in $CD_3CN$ is as follows: 0.93(t, 7.41 Hz, 6H), 1.28(t, 7.36 Hz, 6H), 1.54(m, 4H), 2.60~2.74(m, 12H).

EXAMPLE 5

Determination of Degradation Rate of Bis (n-Propylamine Silver) Diethylthioether Dinitrite by UV Irradiation The organic metal precursor obtained from the above Example 4, bis(n-propylamine silver)diethylthioether dinitrite was exposed to UV light by means of a Hg—Xe lamp with periodically measuring the degradation rate thereof, and the results are shown in FIG. 1. As can be seen from FIG. 1, the organic ligands mostly dissociated from the precursor compound at about 4 minutes after the exposure.

EXAMPLE 6

Figure 2:
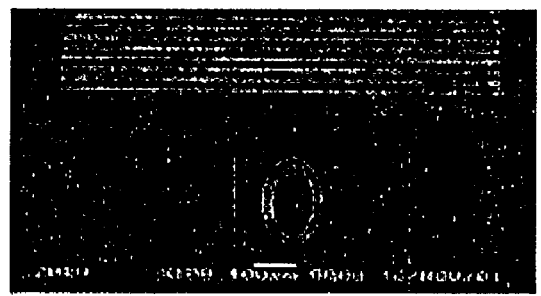
FIG. 2 is a photograph showing the metal pattern formed according to Example 6.

Formation of a Patterned Film of a Metal Using Bis (n-Propylamine Silver) Diethylthioether Dinitrite The organic metal precursor obtained from the above Example 4, bis(n-propylamine silver)diethylthioether dinitrite was dissolved in acetonitrile to 0.3M. The resulting solution was applied to a glass substrate by using a spin coater with maintaining the rotation frequency to 2,000 rpm, to produce a 1 μm thick coating film. The coating film was then covered with a photomask and exposed to light ranging from 200 nm to 800 nm in the wavelength by means of Oriel 60200(200 watts, Oriel, USA). Following the exposure for 4 minutes, the photomask was removed. Thereafter, the coating film was washed with actonitrile so that unexposed areas of the film were removed. The coating film was subjected to reduction with 0.1 mol of hydrazine for 30 seconds, to produce a patterned film of silver. In FIG. 2 are shown the photograph of the pattern. The specific resistance of the silver film was determined as 15 μΩcm.

As stated above, by virtue of the present invention, it has been realized that electroconductive patterned films of a metal can be formed without using photosensitive resins.

The simple modification and change of the present invention will be readily made by persons skilled in the art and it should understood that all of such modification and change are encompassed within the scope of the present invention.

What is claimed is:

1. An organic metal precursor represented by the formula (I):

  (I)

Wherein, M is a transition metal atom selected from the group consisting of Ag, Au, Co, Cu, Pd, Ni, Pt, Zn and Cd;

L is a thioether represented by the formula (II) or (III);

  (II)

wherein in the formula (II), each of $R_1$ and $R_2$, independently, is a $C_{2-20}$ straight-chain, branched-chain or cyclic alkyl, alkenyl or alkynyl group, or an allyl group;

  (III)

in the formula (III), each of $R_3$ and $R_4$, independently, is a hydrogen atom, or a $C_{1-15}$ straight-chain or branched-chain alkyl group, and y is an integer from 2 to 10;

L' is a ligand selected from the group consisting of amines, thiols, selenols and phosphines;

X is an anion selected from the group consisting of halogeno, hydroxide (OH$^-$), cyanide (CN$^-$), nitroxyl (NO$^-$), nitrite (NO$_2^-$), nitrate (NO$_3^-$), azide (N$_3^-$), thiocyanato, isothiocyanato, tetraalkylborate, tetrahaloborate, hexafluorophosphate (PF$_6^-$), triflate (CF$_3$SO$_3^-$), tosylate(Ts$^-$), sulfate(SO$_4^{2-}$), and carbonate (CO$_3^{2-}$);

each of m and n, independently, is an integer from 1 to 10; and each of o and p, independently, is an integer from 0 to 10.

2. The organic metal precursor according to claim 1, wherein each of $R_1$ and $R_2$, independently, is selected from the group consisting of ethyl, propyl, isopropyl, isobutyl and phenyl.

* * * * *